United States Patent
Oetiker et al.

(10) Patent No.: US 6,414,221 B1
(45) Date of Patent: Jul. 2, 2002

(54) TRANSIENTLY ACTIVATED STRESS-INDUCIBLE PLANT PROMOTERS

(75) Inventors: Juerg H. Oetiker, Thermowil (CH); Oy Yin Shiu, Hong Kong (HK); Shang Fa Yang, Davis, CA (US); Win Kin Yip, Hong Kong (HK)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/363,243

(22) Filed: Jul. 28, 1999

(51) Int. Cl.[7] .......................... A01H 1/00; C12N 15/82; C12N 15/87; C12N 5/04; C12N 5/10
(52) U.S. Cl. ...................... 800/287; 800/278; 435/468; 435/419
(58) Field of Search ................................ 800/287, 298, 800/278, 284, 294; 435/252.3, 419, 468, 320.1; 536/23.6, 23.1

(56) References Cited

PUBLICATIONS

Destefano–Beltran et al. characterizationof three members of the ACC Synthase gene family in Solanum tuberosum L. Mol. Gen. Genet. vol. 246 (1995) pp. 496–508.*

* cited by examiner

*Primary Examiner*—Remy Yucel
*Assistant Examiner*—Konstantina Katcheves
(74) *Attorney, Agent, or Firm*—Townsend & Townsend & Crew LLP

(57) ABSTRACT

The present invention provides new rapidly induced promoters. The promoters can be induced in response to various stimuli, such as flooding and wounding.

17 Claims, 1 Drawing Sheet

TRANSIENTLY ACTIVATED STRESS-INDUCIBLE PLANT PROMOTERS

STATEMENT AS TO RIGHTS TO INVENTIONS MADE UNDER FEDERALLY SPONSORED RESEARCH AND DEVELOPMENT

This invention was made with Government support under Grant No. MCB9303801, awarded by the NSF. The Government has certain rights in this invention.

FIELD OF THE INVENTION

This invention relates to field of plant genetic engineering. In particular, it relates to promoters useful for inducible, transient expression of heterologous genes.

BACKGROUND OF THE INVENTION

In the production of transgenic plants it is extremely valuable to have a variety of plant promoters that can be induced in response to various environmental stimuli. Currently, most inducible plant promoters are induced by application of chemicals. For example, plant promoters induced by tetracyline (Caddick et al. *Nature Biotechnology* 16:177–180 (1998)), dexamethasone (Gatz, *Annu. Rev. Plant Physiol. Plant Mol. Bio.* 48:89–108 (1997)) and ethanol (Aoyoma et al. *Plant Journal* 11:605–612 (1997)) are known. Identification of plant promoters induced by non-chemical stimuli would be extremely useful.

One of the most common plant responses to wounding or flooding is the induction of ethylene synthesis. Ethylene plays an important role in plant growth and development, including the control of seed germination, leaf senescence, floral fading, senescence and fruit ripening. Besides the stimulation by internal factors, ethylene synthesis is also stimulated by external factors. These include the induction of ethylene by chemicals and stresses, such as the attack by pathogens and environmental stresses, such as pollution, drought, chilling, heating, wounding and water logging, i.e. the soil flooding of plants (Jackson, M. B. *Annu. Rev.Plant Physiol.*, 36, 145–175 (1985); Abeles et al., *Ethylene in Plant Biology*, Ed. 2, Academic Press, San Diego (1994)).

Ethylene is synthesized from S-adenosylmethionine via 1-aminocyclopropane-1-carboxylic acid (ACC), the immediate precursor of ethylene (Adams, D. Q. and Yang, S. F., *Proc. Natl. Acad. Sci. USA*, 76, 170–174 (1979)). The reactions are catalyzed by ACC synthase (ACS), the key enzyme of ethylene synthesis and ACC oxidase (ACO) (Kende H, *Annu. Rev. Plant Physiol.*, 44, 283–307 (1993)).

Flooded tomato roots synthesize the ethylene precursor ACC which is transported via the xylem to the leaves within 6 to 12 hours (Bradford K J. and Yang S. F., *Plant Physiol.*, 65, 322–326 (1980)). The ethylene produced by waterlogged plants can be interpreted as an early warning of deteriorating soil conditions, inducing changes above ground to increase stress tolerance. Anaerobiotic conditions caused by flooding induce transcription of ACC synthase mRNAs in roots (Zarembinski T. I. and Theologis A., *Mol. Biol. Cell* 4, 363–373 (1993); Olson et al., *J. Biol. Chem.*, 270, 14056–14061 (1995); Zarembinski, T. I. and Theologis, A. *Plant Mol. Biol.*, 33, 71–77 (1997)). ACC synthase is encoded by a multigene family and in the tomato seven members of this gene family, LE-ACS1a, 1b, 2, 3, 4, 5 and 6 are known and differentially expressed (Van der Straeten et al.,*Proc.Natl.Acad.Sci. USA*, 87,4859–4863 (1990); Rottmann et al., *J.Mol.Biol.*, 222, 937–961 (1991); Olson et al., *Proc. Nat. Acad. Sci. USA* 88, 5340–5344 (1991); Yip et al., *Proc. Natl. Acad. Sci. USA*, 89, 2475–2479 (1992); Oetiker et al., *Plant Mol. Biol.*, 34, 275–286 (1997)).

The gene LE-ACS2, commonly known as the ACC synthase that causes fruit ripening is induced in flooded roots (Van der Straeten et al., *Proc.Natl.Acad.Sci. USA*, 87,4859–4863 (1990); Rottmann et al., *J.Mol.Biol.*, 222, 937–961 (1991); Parsons B. L. and Mattoo A. K., *Plant Mol. Biol.*, 17, 453–464 (1991); Oeller, *Science*, 254, 437–439 (1991); Olson et al., *J. Biol. Chem.*, 270, 14056–14061 (1995)). However, LE-ACS2 cannot be solely responsible for flooding induced ethylene because ACC is delivered from root to shoot within 6 to 12 hours after flooding but the LE-ACS2 transcript appears only 8 hours after flooding of the roots (Bradford K J. and Yang S. F., *Plant Physiol.*, 65, 322–326 (1980); English, et al., *J. Exp. Botany* 45, 33.–33. (1995); English et al., *Plant Physiol.*, 109, 1435–1440 (1995))(Olson et al., *J. Biol. Chem.*, 270, 14056–14061 (1995)). LE-ACS3 is also induced in flooded tomato roots, but half of its polyadenylated mRNA remains unspliced, a commonly observed phenomenon under anaerobiotic stress (Olson et al., *J. Biol. Chem.*, 270, 14056–14061 (1995)). Such stress-induced splicing failures will not lead to a functional ACS protein and therefore, we were looking for further ACS transcripts, potentially responsible for the initial burst of ethylene produced by leaves of waterlogged plants.

Identification of plant genes induced by flooding or other environmental stresses would be useful in isolation and preparation of inducible plant promoters. For example, identification of new inducible promoters that are induced quickly and provide transient expression of heterologous nucleic acids would extremely useful in controlling plant responses to various environmental stimuli. The present invention addresses these and other needs.

SUMMARY OF THE INVENTION

The present invention provides recombinant expression cassettes comprising an ACS7 promoter operably linked to a heterologous polynucleotide sequence. The promoter is at least about 70% identical to SEQ ID NO:1, the LE-ACS7 promoter from tomato. The heterologous polynucleotide sequence is not critical part of the invention. In some embodiments, the polynucleotide encodes a polypeptide, for example, one that confers resistance to a plant pathogen. Alternatively, the heterologous polynucleotide can be operably linked to the ACS7 promoter in the antisense orientation.

The recombinant expression cassettes of the invention are typically incorporated into vectors suitable for production of transgenic plants. The vector will usually further comprise an independent terminator sequence, replication sequences and a selection marker sequence. The expression cassettes of the invention can also be incorporated into the genome of transgenic plant. Thus, the invention also provides transgenic plants comprising the recombinant expression cassette of the invention. The transgenic plant can be any species, for example, tomato.

The invention also provides methods of expressing a nucleic acid in a plant. The methods comprise providing a transgenic plant comprising a recombinant expression cassette of the invention, and subjecting the plant to an environmental stimulus which activates the ACS7 promoter, thereby transcribing the heterologous nucleic acid. The environmental stimulus is typically flooding or wounding.

Definitions

The term "stress" refers to harm or damage done to organs and/or tissues of a plant, including the roots, stems, leaves, buds, etc. The cause of stress can be exposure of the plant to anaerobic conditions (e.g., as a result of flooding), wounding, (e.g., cutting, scraping, freezing, and pinching), exposure to chemicals, (e.g. herbicides, fungicides, and insecticides), exposure to pathogens, (e.g., bacteria, viruses, and fungi), or exposure to pests, (e.g. insects, and nematodes), and the like.

The term "promoter" refers to regions or sequence located upstream and/or downstream from the start of transcription and which are involved in recognition and binding of RNA polymerase and other proteins to initiate transcription. A "plant promoter" is a promoter capable of initiating transcription in plant cells. Such a promoter can be derived from plant genes or from other organisms, such as viruses capable of infecting plant cells.

An "ACS7 promoter" refers to a plant promoter capable of initiating transcription from an operably linked heterologous sequence and which is at least substantially identical to the promoter sequence in SEQ ID NO:1 (LE-ACS7, from tomato). The promoters of the invention need not be full length, the promoters are typically from about 1000 to about 2500 nucleotides in length, usually from about 1500 to about 2000 nucleotides and often between about 2300 and about 2450 nucleotides.

A polynucleotide sequence is "heterologous to" a second polynucleotide sequence if it originates from a different gene, or, if from the same gene, is modified from its original form. For example, a promoter operably linked to a heterologous coding sequence refers to a coding sequence from a gene different from that from which the promoter was derived, or, if from the same gene, a coding sequence which is not naturally *associated with the promoter (e.g. a genetically engineered coding sequence or an allele from a different ecotype or variety).

The phrase "operably linked" refers to functional linkage between a promoter and a second sequence, wherein the promoter sequence initiates transcription of RNA corresponding to the second sequence.

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as a $T_1$ (e.g. in Arabidopsis by vacuum infiltration) or $R_0$ (for plants regenerated from transformed cells in vitro) generation transgenic plant. Transgenic plants that arise from sexual cross or by selfing are descendants of such a plant.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art.

Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 70%, more preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403–410 and Altschuel et al. (1977) *Nucleic Acids Res.* 3389–3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Lower stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

DETAILED DESCRIPTION

Figure 1:
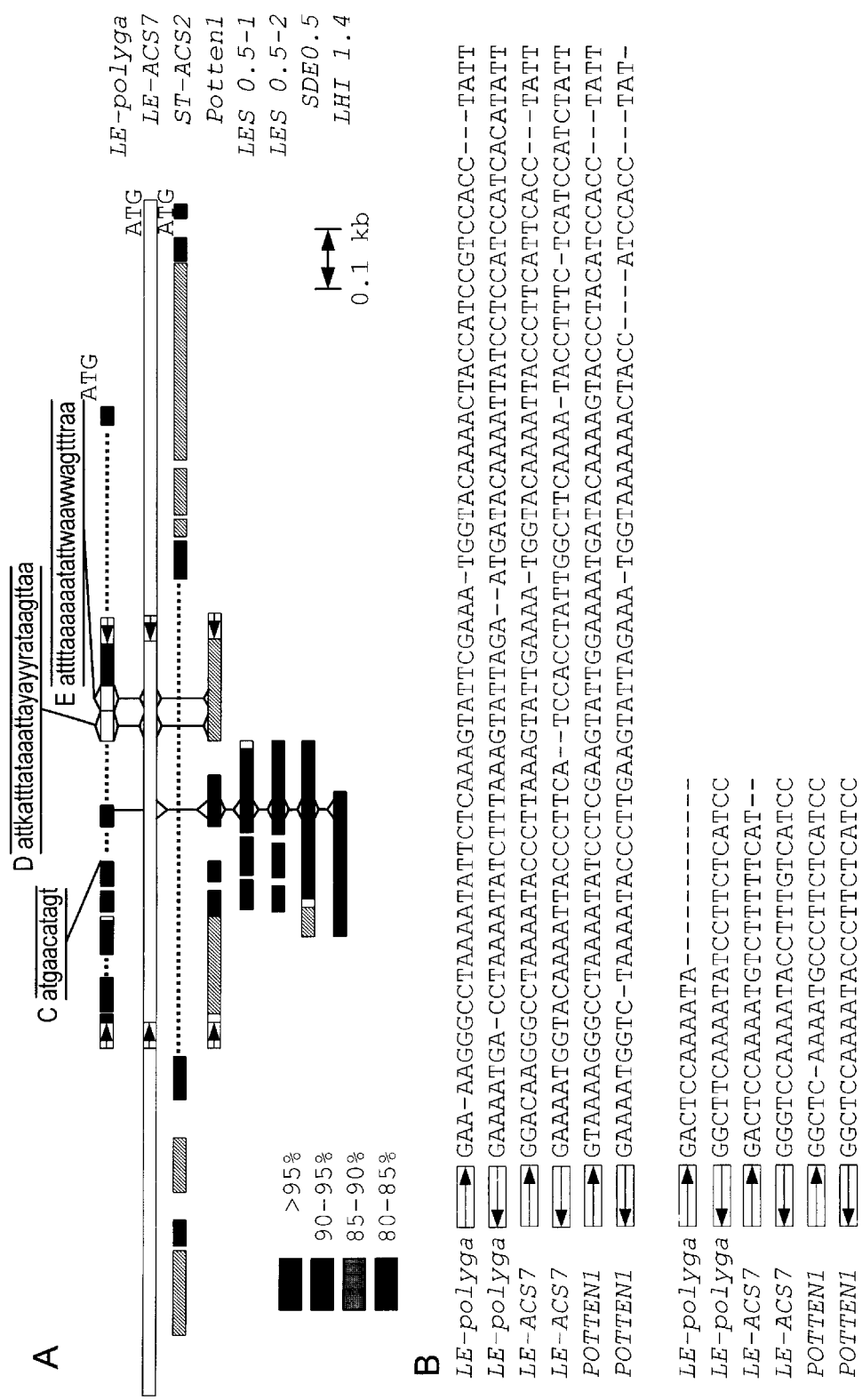
FIG. 1 shows sequence comparisons of the LE-ACS7 promoter with Sol3 elements and plant promoters. The promoter of LE-ACS7 is schematically depicted as a light grey bar, ending with the initiation codon and the scale is indicated by an arrow. Dotted lines in the ST-ACS2 and polygalacturonase (LE-PG) promoters represent gaps that were inserted. Blocks of sequence identity with the LE-ACS7 promoter, as revealed by a gapped BLAST search were plotted above and below the LE-ACS7 promoter at their respective positions. The degree of identity is shown by various gray shadings as indicated, and identities of less than 80% are not shown. The position of the nuclear protein binding DNA sequences C, D and E (SEQ ID NOS:4–6) in the positive regulatory region of the PG promoter (nucleotides −412 to −806) and their consensus sequence with LE-ACS7 are shown. Region C is partially truncated in LE-ACS7. Vertical lines show where these regions are located on the LE-ACS7 promoter and their position on various Sol3 elements. The Sol3 DNA sequences used are: from *Solanum tuberosum* (Potten1) Genbank accession Nr U91987; *Solanum demissum* (SDE 0.5) Genbank accession Nr. U91992; *Lycopersicon esculentum* (LES 0.5–1), accession U91989; (LES 0.5–2), accession U91990.

The present invention is based, at least in part, on the identification of a novel class of ACC synthase genes, ACS7, exemplified by the LE-ACS7 gene in tomato. This gene is rapidly and transiently induced in waterlogged roots and in wounded leaves. In combination with LE-ACS2, the LE-ACS7 transcript forms a rhythmic pattern that slightly precedes the diurnal fluctuation of ethylene synthesis by leaves of the flooded plants. Thus, the invention provides a new class of inducible promoters that provide transient expression of a desired protein or mRNA within minutes of the stimulus. In addition, the promoters can be induced by environmental stresses, such as flooding or wounding, without the application of chemicals.

Making Recombinant Expression Cassettes

The ACS7 promoters of the invention are recombinantly fused to a heterologous nucleic acid to prepare recombinant expression cassettes. The promoters of the invention are particularly useful for situations in which rapid, inducible, transient expression of heterologous nucleic acid sequences is desired. Typically, the sequence will encode a desired protein. Alternatively, the sequence may be used to transcribe an mRNA that is not translated into a protein (e.g. antisense RNA or ribozymes).

Methods of recombinantly joining nucleic acids, including cloning, in vitro ligation, and the like, are well known. Examples of appropriate recombinant techniques, including restriction enzyme digestion, ligation of nucleic acids, cloning, sequencing and the like, sufficient to direct persons of skill are found, for instance, in Berger and Kimmel, *Guide to Molecular Cloning Techniques*, METHODS IN ENZYMOLOGY Vol. 152 Academic Press, Inc., San Diego, Calif. (Berger) and in Sambrook et al. MOLECULAR CLONING—A LABORATORY MANUAL (2nd ed.) Vol. 1–3 (1989) (Sambrook) and in CURRENT PROTOCOLS IN MOLECULAR BIOLOGY, Ausubel, F. M., et aL, eds., Greene Publishing Associates, Inc. and John Wiley & Sons, Inc., (1996 Supplement) (Ausubel).

In vitro amplification techniques suitable for amplifying nucleic acids for use as molecular probes or generating nucleic acid fragments for subsequent subcloning are well known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as U.S. Pat. No. 4,683,202; PCR PROTOCOLS A GUIDE TO METHODS AND APPLICATIONS, Innis et al. eds., Academic Press Inc. San Diego, Calif. (1990) (Innis); Amheim & Levinson (Oct. 1, 1990) *C&EN* 36–47; Kwoh, et al., *Proc. Natl. Acad. Sci. USA* 86:1173 (1989); Guatelli, et al., *Proc. Natl. Acad. Sci. USA* 87:1874 (1990); Lomell, et al., *J. Clin. Chem* 35:1826 (1989); Landegren, et al., *Science* 241:1077 (1988); Van Brunt, *Biotechnology* 8:,291 (1990); Wu & Wallace, *Gene* 4:560 (1989); Barringer, et al. *Gene* 89:17 (1990) and Sooknanan & Malek, *Biotechnology* 13:563 (1995). Improved methods of cloning in vitro amplified nucleic acids are described in U.S. Pat. No. 5,426,039.

Oligonucleotides for use as probes, e.g., in in vitro amplification methods and for use as gene probes are typically synthesized chemically according to the solid phase phosphoramidite triester method described by Beaucage & Caruthers, *Tetrahedron Lett.* 22:1859–1862 (1981).

The particular heterologous nucleic acid sequence used in the expression cassettes of the invention is not a critical aspect of the invention. The promoters are also useful in the expression of desired nucleic acids in roots, particularly in response to flooding. The expressed gene may be, for example, one that enhances the plant's response to anaerobic stress caused by flooding. Genes known to enhance survival of anaerobic conditions (e.g. alcohol dehydrogenase) can be used for this purpose.

Alternatively, the flooding can be used as the stimulus that induces the desired sequence. Thus, simply flooding the plant can be used in place of application of chemicals to induce a desired response. Thus, flooding can be used to induce transient production of nutrient uptake related proteins (e.g. transporters and ion pumps), or enzymes involved in the biosynthesis of desired compounds that are eventually transported to the shoot.

The encoded proteins can also enhance the ability of the plant to stress. These proteins can be autologous, heterologous but still derived from plants, or from organisms other than plants, for example animals, bacteria, or fungi.

For example, the promoters of the invention can be used to induce expression of genes that control insect pests or pathogens (bacteria and fungi), such that the protein is only produced shortly after the first bites of the insect and transiently so as to decrease selective pressure for resistant insects. For example, to resist insect infestations, the plants can be engineered to express *Bacillus thuringiensis* toxin (see Vacek, et al., *Nature* 232:732 (1986)). Alternatively, the promoters can be used to express coat proteins from viruses (see, Abel, et al. in *Science* 232:738 (1986)) U.S. Pat. No. 5,614,395 describes a family of small pathogenesis related proteins that are expressed by plants undergoing a pathogenic injury. Other exemplary proteins include chitinases (see, U.S. Pat. No. 5,530,187) to inhibit fungal infections, phytoalexins, and the like.

To confer resistance to herbicides, the transgenic plants of the invention are optionally engineered to express acetohydroxy acid synthase, which has been found to provide plants which overexpress this enzyme resistance to multiple types of herbicides (see, Hattori, J., et al., *Mol. Gen. Genet.* 246(4):419 (1995). Other proteins that have been found to confer resistance to herbicides include: a chimeric proteins of rat cytochrome p4507A1 and yeast NADPH-cytochrome P450 oxidoreductase (Shiota, et al., *Plant Physiol.* 106(1)17 (1994) and phosphotransferases (Datta, et al., *Plant Mol. Biol.* 20(4):619 (1992). Glutathione reductase and superoxide dismutase (Aono, et al., *Plant Cell Physiol.* 36(8):1687 (1995), have been found to confer resistance to fungal toxins and oxidative stress in cold, salinity, drought and wounding.

As noted above, the operably linked polynucleotide sequence need not encode a protein. Thus, the expression cassettes can be used to block the translation of a selected cellular mRNA. Antisense RNA inhibition of gene expression has been shown; see, e.g., Sheehy, et al., *Proc. Nat'l. Acad. Sci. USA* 85:8805 (1988), and U.S. Pat. No. 4,801, 340. In addition to antisense suppression, sense suppression of genes is also used to inhibit mRNA expression. For examples of the use of sense suppression to modulate expression of endogenous genes see, Napoli, et al., *The Plant Cell* 2:279 (1990) and U.S. Pat. No. 5,034,323. Catalytic RNA molecules or ribozymes can also be used to inhibit gene expression. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true nucleic acid enzyme. The inclusion of ribozyme sequences within antisense RNAs confers RNA-cleaving activity upon them, thereby increasing the activity of the constructs (see, Castanotto, et al, *Advances in Pharmacology* 25:289 (1994) and the references therein provides an overview of ribozymes in general, including group I ribozymes, hammerhead ribozyrnes, hairpin ribozymes, RNAse P, and axhead ribozymes. See also, Haseloff, et al., *Nature* 334:585 (1988). Examples of GUA cleaving ribozyme genes based on the negative strand satellite RNA of the Arabis Mosaic Virus are described in De Young, et al., *Biochemistry* 34:15785 (1995).

Making Transgenic Plants

The DNA constructs of the invention may be introduced into plant cells, either in culture or in organs of a plant, e.g., leaves, stems, fruit, etc. The expression of natural or synthetic nucleic acids can be achieved by operably linking a nucleic acid of interest to the ACS7 promoter, incorporating the construct into an expression vector, and introducing the vector into a suitable host cell.

Typical vectors contain transcription and translation terminators, transcription and translation initiation sequences, and promoters useful for regulation of the expression of the particular nucleic acid, i.e., ACS7 promoters of the invention. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature*, 328:731 (1987); Schneider, B., et al., *Protein Expr. Purif.* 6435:10 (1995); Berger & Kimmel; Sambrook and Ausubel.

The DNA constructs of the invention are introduced into plant cells, either in culture or in the organs of a plant by a variety of conventional techniques. For example, the DNA construct can be introduced directly into the genomic DNA of the plant cell using techniques such as electroporation and microinjection of plant cell protoplasts, or the DNA constructs can be introduced directly to plant cells using ballistic methods, such as DNA particle bombardment. Alternatively, the DNA constructs are combined with suitable T-DNA flanking regions and introduced into a conventional *Agrobacterium tumefaciens* host vector. The virulence functions of the *Agrobacterium tumefaciens* host directs the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski, et al., *EMBO J.* 3:2717 (1984). Electroporation techniques are described in Fromm, et al., *Proc. Nat'l. Acad. Sci. USA* 82:5824 (1985). Ballistic transformation techniques are described in Klein, et al., *Nature* 327:70–73 (1987).

Agrobacterium tumefaciens-mediated transformation techniques, including disarming and use of binary vectors, are also well described in the scientific literature. See, for example Horsch, et al., *Science* 233:496–498 (1984), and Fraley, et al., *Proc. Nat'l. Acad. Sci. USA* 80:4803 (1983). Agrobacterium-mediated transformation is a preferred method of transformation of dicots.

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., PROTOPLASTS ISOLATION AND CULTURE, HANDBOOK OF PLANT CELL CULTURE, pp. 124–176, Macmillian Publishing Company, New York, (1983); and Binding, REGENERATION OF PLANTS, PLANT PROTOPLASTS, pp. 21–73, CRC Press, Boca Raton, (1985). Regeneration can also be obtained from plant callus, explants, somatic embryos (Dandekar, et al., *J.*

*Tissue Cult. Meth.* 12:145 (1989); McGranahan, et al., *Plant Cell Rep.* 8:512 (1990)), organs, or parts thereof. Such regeneration techniques are described generally in Klee, et al., *Ann. Rev. of Plant Phys.* 38:467–486 (1987).

The nucleic acids of the invention can be used to confer desired traits on essentially any plant. Thus, the invention has use over a broad range of plants, including species from the genera Asparagus, Avena, Brassica, Citrus, Citrullus, Capsicum, Cucumis, Cucurbita, Daucus, Fragaria, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna, and Zea. The ACS7 promoters of the invention are particularly useful in the production of transgenic plants in the genus Lycopersicon.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Measuring ACS7 Promoter Activity

ACS7 promoter activity can be determined by measuring the difference upon flooding, wounding or other stimulus in mRNA transcribed by genes under the control of the ACS7 promoter. Alternatively, the level of protein produced from this transcribed RNA. can be determined before and after wounding.

For example, promoter activity can be measured in a quantitative northern blot which directly measures the amount of mRNA in a selected biological sample which is transcribed from a gene regulated by the promoter. Performing quantitative northern blot analysis is well known. Similarly, the level of RNA can be measured indirectly using quantitative PCR. In addition to measuring RNA levels, the level of protein encoded by an RNA can also be measured. Typically, this is suitably performed for proteins which are not translationally regulated, so that the level of protein corresponds to the amount of RNA which is transcribed from a gene under the control of a promoter. Protein determinations are routine in the art, commonly being performed by western blot analysis, ELISA or other affinity detection techniques which monitor the level of protein in a sample. See, Coligan, CURRENT PROTOCOLS IN IMMUNOLOGY, Wiley/Greene, N.Y. (1991); and Harlow & Lane, ANTIBODIES: A LABORATORY MANUAL, Cold Spring Harbor Press, N.Y. (1989). See also, Ausubel, supra.

The level of induction of a promoter by an environmental stimulus refers to the percent or fold increase in the production of transcribed or translated gene products under the control of a promoter in response to a stimulus. Preferred ACS7 promoters in transgenic plants comprising the promoters are induced at least about 5-fold, generally at least about 10-fold, often at least about 50-fold, and preferably at least about 100-fold in response to flooding or wounding of the plant.

EXAMPLES

The following examples are offered to illustrate, but no to limit the claimed invention. The methods described below are as set forth in Shiu et al. *Proc Natl Acad Sci USA* 95:10334–9 (1998).

MATERIALS AND METHODS

Plant Material

Tomato plants (*Lycopersicon esculentum* Mill., cv. UC82) were grown in pots of 15 cm diameter in a greenhouse under standard conditions. Ten-week-old plants were used for the experiments. Fruits were harvested at the stages mature green, turning, pink, orange and red and the pericarp was used for RNA extraction. A suspension culture of cv. VFTN was maintained as described (Oetiker et al., *Plant Mol. Bid.*, 34, 275–286 (1997)).

Induction of Ethylene Synthesis

Young mature leaves were punched with a brass wire brush and detached after 0, 1, 2, 4, 6 and 8 hours. The collected leaf tissues were divided into two portions, one part was assayed for ethylene production and the second part was quick-frozen for later RNA extraction. For wounding of stems and roots, the isolated tissues were cut into 5 mm long pieces and incubated on a moist filter paper in a petri-dish for 6 h. For flooding, the roots were submerged in water for 0 to 260 hours. Leaves and roots were collected and part of them either quick-frozen for subsequent RNA extraction or immediately assayed for ethylene production and ACC content. For ethylene treatment, plants were incubated in sealed containers with 10 ppm $C_2H_4$ for 12 h and the tissues then quick-frozen for RNA extraction. For elicitor treatment, the suspension cultured cells were incubated for 1 h in the presence of 200 μg/ml yeast elicitor. For auxin treatment, 5 mm sections from the top third of the hypocotyl of 7-day-old etiolated seedlings were floated on 10 μM NAA for 90 min.

Ethylene determination

Either the third youngest mature leaf or the root were used to determine ethylene production, following the procedure of Jackson and Campbell (*Planta*, 129, 273–274 (1976)). The excised tissues were weighed and capped into a 50 ml Erlenmeyer flask. After 30 minutes a 1 ml gas sample was withdrawn and analyzed by gas chromatography.

ACC determination

Leaf or root tissues were extracted twice with 5 ml of 80% ethanol at 70° C. for 30 minutes. The combined extracts were evaporated in vacuo and the residue dissolved in 1 ml of distilled water. ACC was determined according to Lizada and Yang (*Anal. Biochem.* 100:140–145 (1979)). The assay was carried out in a 15 ml test tube with 1 ml reaction mixture containing the ACC extract, 5 μmol $HgCl_2$ and 5% NaOCl and saturated NaOH (2:1; v/v) at 0° C. The mixture was vortexed for 10 seconds and a 1 ml gas sample was removed for ethylene determination. An internal standard was assayed together with every sample.

Nucleic acid extraction

Total RNA was extracted according to the method of Plant Molecular Biology Manual (Katharina et al,. Isolation of total, poly(A) and polysomal RNA from plant tissues. In *Plant Molecular Biology Manual*, Vol. 1, pp 1–4 (S. B. Gelvin and R. A. Schilperoort, eds.) Kluwer Academic Publishers (1995)) with some modifications. The tissues were ground to a fine powder in liquid nitrogen and extracted with a mixture of phenol and extraction buffer (1:1, v/v) at 90° C. The supernatant was partitioned against chloroform and then precipitated twice with 2M LiCl. The nucleic acids were precipitated in 0.3M sodium acetate (pH 5.4) and 2.5 volumes of ethanol at −20° C. overnight. Genomic DNA was isolated according to Plant Molecular Biology Manual (Katharina et al,. Isolation of total, poly(A) and polysomal RNA from plant tissues. In *Plant Molecular Biology Manual*, Vol. 1, pp 1–4 (S. B. Gelvin and R. A. Schilperoort, eds.) Kluwer Academic Publishers (1995)).

Reverse Transcriptase (RT) PCR and PCR

Five μg of total RNA were annealed with 1 μg of oligo-dT in 0.3M NaCl, 3 mM EDTA, 10 mM Tris-HCl, pH 7.5 and 1 μl of RNAs in (Promega) at 50° C. for 30 minutes. The mixture was adjusted to 1 mM of each d-NTP's, 1 mM DTT, 10 mM Tris-HCl, pH8.4, 6 mM $MgCl_2$ and 60 μg/ml actinomycin D in a final volume of 40 μl. Fifty units of AMV reverse transcriptase were added and the mixture was incubated at 42° C. for 2 hours. The nucleic acids were precipitated and resuspended in 250 μl DEPC-treated water. The PCR was done using 5 μl of this solution and Taq polymerase (Perkin-Elmer Cetus) according to the specifications of the manufacturer. The primers used for amplification were (A) AYCCWTSWAATCCAYTRGGNAC (SEQ ID NO:13) and (B) ACWARNCCRAARCTNGACAT (SEQ ID NO:14), corresponding to two conserved blocks, referred to as 4 and 6, of ACC synthase (see Dong et al., *Planta* 185, 38–45 (1991) for nomenclature). The primers used for amplification of genomic DNA were (C) CATGGCTAGCA-CAAAATCCAGA (SEQ ID NO:15) (corresponding to nt 2685–2707 of FIG. 3 of (Olson et al., *J. Biol. Chem.*, 270, 14056–14061 (1995)) and (D) TACACTGATGTATGG-GATAGAGTTCA (SEQ ID NO:16) (reverse complement of nt 3425–3451 of SEQ ID NO:2.

Ribonuclease Protection Assay

The plasmids used as probes in the RPA assay were pBTAS1, pBTAS2 (Yip et al., *Proc. Natl. Acad. Sci. USA*, 89, 2475–2479 (1992)) and pCS14HP (corresponding to nts 3202 to 3494 of SEQ ID NO:2), corresponding to the tomato ACC synthase genes LE-ACS2, LE-ACS3 and LE-ACS7, respectively. The plasmids were linearized with restriction enzymes to give 5'-overhanging ends and radioactive RNA probes were prepared by in vitro transcription with T7 RNA polymerase at 37° C. for 1 hour in the presence of 70 μCi of $^{32}$P-UTP (Amersham). The transcripts were purified in a 5% acrylamide/8M urea gel. The RPA assay was carried out with the High-Speed hybridization RPA assay kit from Ambion (Houston, Tex., USA) according to the instructions of the manufacturer. The fragments were separated in a 5% acrylamide/8M urea gel. The gel was transferred to a Whatman 3MM paper and exposed to an X-ray film with a pair of intensifying screens at −80° C. overnight.

Genomic cloning and DNA sequencing

Tomato genomic libraries cloned into λ-EMBL3 were from Clontech (Palo Alto, Calif. USA) or a kind gift provided by Dr. Charles S. Gasser (UC Davis, Calif.) (Budelier et al., *Mol. Gen. Genet.*, 224, 183–192 (1990)). Plating, plaque lifting and filter hybridization were done according to standard procedures (Maniatis et al., Molecular Cloning: a Laboratory Manual Laboratory (1990)). The purified 800 bp EcoRI insert of p4ROM2 was labeled with [α-$^{32}$P]-dATP (Amersham, Buckinghamshire, UK) and used as a probe for library screening. Positively hybridizing λ-EMBL3 clones were isolated, purified, digested with Hindlll and the fragments were subcloned into pBluescript II SK$^+$ (Stratagene). Selected subclones were sequenced in both directions by dideoxy-sequencing using Sequenase 2.0 (United States Biochemical), universal or synthetic primers and $^{35}$S-dATP (Amersham, Buckinghamshire, UK). Sequence analyses were performed with the PC/GENE software (Intelligenetics).

RESULTS

Isolation, Cloning and Characterization of ACS7

A combination of RT-PCR and subtraction by restriction enzyme digestion lead to the isolation of this tomato ACC synthase gene. Twelve first strand cDNA libraries, prepared from intact, wounded and ethylene-treated roots, stems and leaves, auxin-treated hypocotyl sections, elicitor-treated suspension culture and fruit pericarp at five different ripening stages were individually amplified with two primers called A and B, corresponding to two conserved blocks, referred to as 4 and 6, described in Dong et al., (*Planta* 185, 38–45

(1991)). To eliminate known ACS transcripts, the PCR products were combined and sequentially digested with BclI, AccI, AvaI, StyI and ClaI. These enzymes specifically recognize a site centered between blocks 4 and 6 of LE-ACS1A and 1B, LE-ACS2, LE-ACS3, LE-ACS4 and LE-ACS5, respectively. Fragments that remained uncut were cloned and sequenced. One clone, p4ROM1, revealed an overall sequence similarity of 80% with intermittent stretches of complete identity to the corresponding region of LE-ACS3. It contained none of the above recognition sites and represented a novel ACC synthase, designated LE-ACS7. For screening of genomic libraries a probe more divergent from LE-ACS3 was obtained by amplification of genomic tomato DNA with two different primers, called D and C, D being specific for LE-ACS7, and C having been experimentally selected from a number of forward primers previously used for sequencing LE-ACS3 and cross annealing to LE-ACS7. The coding region of the resulting 818 nt PCR-clone, p4ROM2 was less similar (72% ) and contained two introns very divergent from those of LE-ACS3. 500,000 plaques from a tomato genomic library were screened with p4ROM2 and positively hybridizing clones were selected after four screens, resulting in the λ-EMBL3 clone, pLPT1, containing the complete LE-ACS7 gene.

The LE-ACS7 Gene

LE-A CS7 encodes a protein of 467 amino acid residues with a molecular weight of 53.1 kd and a pI of 8.3 (SEQ ID NO:3). The seven conserved regions common to all ACC synthases and eleven invariant amino acids conserved in various aminotransferases are also found in this protein (Dong et al., *Planta* 185, 38–45 (1991); Mehta P. K. and Christen P., *Biochem.Biophys.Res. Commun.* 198, 138–143 (1994)). The active site center dodecapeptide sequence is identical to the minor of two peptides isolated earlier from the tomato fruit (Yip et al., *Proc. Natl. Acad. Sci. U.S.A.*, 87, 7930–7934 (1990)). The coding sequence of LE-ACS7 is interrupted by two introns. This gene is highly homologous to LE-ACS3 and represents a class III ACC synthase, which is the class with the highest pI. Phylogenetic analysis of the coding region further revealed that it is most identical to the potato ACC synthase ST-ACS2. LE-ACS7 mapped to the bottom of tomato chromosome 2, between the genetic markers TG31 and CT1O6A, a location that does not coincide with any known tomato mutant phenotypes.

LE-ACS7 is Induced Early After Flooding

Since preliminary experiments revealed that LE-ACS7 is expressed in roots, the role of this gene in flooding was investigated. The flooding treatments started at 8 a.m. and after 1 h the leaves exhibited a steep increase of ethylene production that peaked during mid-day. Subsequently, the rate of ethylene synthesis dropped, and fluctuated in a similar rhythm with second and third maxima after 24 h and 48 h. These peaks coincided with the light periods. In subsequent measurements after 5 and 10 d of flooding, and at daytime, the rate of ethylene synthesis remained high. In contrast, the amount of ethylene released by roots remained at a basal level during the first two days of flooding. After that, when the plants showed severe symptoms, there was an increased rate of ethylene production which at all times was less than 1/10 of the ethylene biosynthetic rate observed in leaves. Apart from an initial increase, the ACC content in leaves remained low and constant. However, the ACC content of flooded roots was higher than in leaves and fluctuated. Clear morphological alterations were noted such as epinasty and the formation of aerial roots on lower stems, and after prolonged flooding, yellowing and senescence of leaves. Besides LE-ACS7, the expression of LE-ACS2 and LE-ACS3, but not of LE-ACS4 and LE-ACS5 which are not induced in flooded roots, was also analyzed (Olson et al., *J. Biol. Chem.*, 270, 14056–14061 (1995)). The transcripts of LE-ACS2, LE-ACS3 and LE-ACS7 were not present in leaves of flooded plants, the tissues with the highest rate of ethylene synthesis. In contrast, they were found in flooded roots. LE-ACS2 was induced 8 h after flooding. Interestingly, this transcript fluctuated, it became reduced after 12 h and increased again after 24 h. The peaks of maximal LE-ACS2 transcript abundance in the roots coincided with the dark periods when the ethylene production of the leaves was low. A minor amount of LE-ACS3 was detectable in unflooded roots and flooding strongly induced that transcript. Two bands were noted in all RPA assays and the abundance of LE-ACS3 remained high at all times. Like LE-ACS3, there was a basal level of LE-ACS7. LE-ACS7 was rapidly induced at the early stages of flooding, preceding the initial peak of flooding-induced ethylene synthesis in the leaves, but it became less abundant after 12 h. The absence of these transcripts in leaves of flooded plants led to the question of whether they cannot express these transcripts at all or if they produce them when challenged by a different stress. In several wounding experiments, ethylene production peaked 2 h after wounding and then decreased (data not shown). LE-ACS2, known to be wound-inducible in the fruit, was not detectable in wounded leaves, and neither was LE-ACS3. However, there was a transient increase of LE-ACS7 mRNA, early after the wounding of leaves suggesting that this gene is involved in the formation of wound ethylene by vegetative tissues and with an expression pattern resembling the one of LE-ACS7 in flooded roots.

The promoter of LE-ACS7 is Tagged by a Sol3 Element

The promoter of LE-ACS7 revealed an exceptionally high degree of similarity over more than 1 kb to the promoter of the wound-repressed potato ACC synthase ST-ACS2. However, the LE-ACS7 promoter contains an insertion of 950 bp not present in ST-ACS2. This insertion is very similar to a region in the promoter of the tomato polygalacturonase (PG) gene that has been shown by deletion analysis to contain positive regulatory regions and, by DNase 1 footprinting, the nuclear protein-binding regions designated C, D and E (FIG. 1A) (Montgomery et al., 1993). This 852 nt long region of the PG promoter was subsequently shown to be a transposon of the Sol3 type (Oosumi et al., *Proc. Natl. Acad. Sci. USA*, 92, 8886–8890 (1995)), a solanaceous transposon family that occurs in tomato and potato, but not in the tobacco (Oosumi, T., Belknap, W. R., *J. Mol. Evol.*, 45, 137–144 (1997a); Oosumi T. and Belknap W. R., *J. Mol. Evol.* 45, 137–144 (1997b)). The LE-ACS7 promoter contains domains similar to the regions C, D and E of the PG promoter (FIG. 1A). Several Sol3 elements occurring in wild forms of the potato and tomato are highly similar to the insert in the LE-ACS7 promoter and also contain domains corresponding to C, D and E. The long terminal inverted repeats that define Sol3 elements were also found in LE-ACS7 and are flanking the Sol3 region (FIG. 1B)(SEQ ID NOS:7–12). The element in the LE-ACS7 promoter was designated LEACS7Sol3.

DISCUSSION

The isolation, genomic cloning and characterization of a novel tomato 1-aminocyclopropane-1-carboxylate (ACC) synthase gene, LE-ACS7 is reported herein. This ACC synthase is involved early in the production of flooding-induced ethylene and is the first tomato ACC synthase gene shown to be induced after wounding of vegetative tomato tissues. Wounding-induced LE-ACS7 transcript accumulation was transient and preceded the production of wound ethylene. The phylogenetically closely related ACC synthase, ST-A CS2 is transiently wound repressed. and it lacks the Sol3 element present in the LE-ACS7 promoter. LE-ACS7 is induced early after flooding, indicating that it is involved as a primary gene in root to shoot communication of flooded tomato plants.

Flooding-induced ethylene produced by the leaves fluctuated and peaked during the light periods when transpiration is high, a phenomenon previously observed in flooded tomatoes (Jackson et al., *J. Exp. Botany* 29, 183–193 (1978)). If the production rate of ACC in roots remained constant after the onset of flooding, one would expect that ACC in the roots accumulates during the dark periods, when transpiration is low. However, the ACC content of roots was high during the day and dropped at night, indicating that the ACC synthase activity in roots, once induced by flooding, may fluctuate in a diurnal rhythm. One possible mechanism for that would be via the transcriptional regulation of the ACC synthase genes. If so, the continuously induced LE-ACS3 would contribute little to the total ACC synthase activity in the roots, in line with a previous observation that much of its flooding-induced mRNA remains unspliced (Olson et al., *J. Biol. Chem.*, 270, 14056–14061 (1995)). Time-controlled synthesis of flooding-induced ACC would conserve nightly resources of the stressed plant, yet provide sufficient substrate during daytime for the LE-ACO1 gene which is induced in the shoots after flooding of the roots (English, et al., *J. Exp. Botany* 45, 33.–33. (1995); English et al., *Plant Physiol.*, 109, 1435–1440 (1995)). Many unflooded plants, including the tomato, show natural rhythms in ethylene evolution with peaks during daylight and the Si-ACO1 ACC oxidase transcript in leaves from Stellaria longipes fluctuates accordingly (Kathiresan et al., *Planta*, 199, 329–335 (1996)). Fluctuation of ACC production of flooded roots may have evolved to most efficiently fit in and exploit the preexisting natural rhythm of the healthy plant to produce flooding-ethylene during daytime. During daytime, it might be most needed to reduce light interception via epinasty in order to maintain the water balance of the flooded plants (Bradford et al., *Plant Physiol.*, 70, 1503–1507 (1982)).

The gene encoding LE-ACS3, was previously cloned and characterized and it was shown to be induced early after flooding and that its promoter contained anaerobiosis response elements (Olson et al., *J. Biol. Chem.*, 270, 14056–14061 (1995)). However, at least half of the LE-ACS3 transcript accumulated as unspliced transcripts and it is unlikely that these stress-induced splicing failures will lead to a fimctional enzyme. LE-ACS4 and LE-ACS5 were not induced in flooded tomato roots. However, LE-ACS2 was induced 10 h after flooding in the tomato variety studied (cv. VFN8). The present study, using cv. UC82B, confirms this result and suggests that signaling for induction of LE-ACS2 in flooded roots is identical in these varieties. The initial burst of flooding-induced ethylene precedes the induction of LE-ACS2, thus other ACC synthase genes must be responsible for the first peak of flooding-induced ethylene. After induction, the abundance of the LE-ACS2 transcript fluctuated, peaked in the nights and preceded the subsequent daily waves of ACC production in roots and the ethylene evolution from shoots. LE-ACS7 was induced early and transiently and could well account, in combination with LE-ACS2, for the observed waves of ethylene production.

Several possibilities may explain the differential induction of these ACC synthase transcripts. For instance, they may be expressed in different root tissues such as the cortex and the central cylinder. The signaling pathway for LE-ACS7 and LE-ACS3 may be identical but differ from the one for late induction of LE-ACS2. Kinetically, it appears that LE-ACS3 and LE-ACS7 directly sense hypoxia in the roots while the delayed and fluctuating induction of LE-ACS2 may be due to a secondary stimulus. Since LE-ACS2 as more abundant during dark periods when transpiration is low, this stimulus might be solutes that accumulate at night. Alternatively, slight increases of the internal ethylene concentration in roots, beyond the limit of detection in the used assays, might be that stimulus. LE-ACS2 is ethylene-inducible in the fruit and responsible for autocatalytic ethylene production (Rottmann et al, *J.Mol.Biol.*, 222, 937–961 (1991); Oeller, *Science*, 254, 437–439 (1991)). The inducible ethylene receptor Nr is also and early induced during fruit ripening, preceding the induction of the ethylene-inducible E8 gene and preventing ripening when mutated (Wilkinson et al., *Science*, 270, 1807–1809 (1995)). Nr is ethylene-inducible in tomato fruits once they have proceeded from the immature green to the mature green stage. The small amounts of ethylene produced by the immature fruit may be involved in that transition (McMurchie et al., *Nature* 237, 235–236 (1972)). The signal for induction of LE-ACS2 and the onset of autocatalytic ethylene production in the fruit maybe transduced via the Nr protein, once the fruit tissue has achieved the developmental competence. Interestingly, flooding also induces the Nr-like ethylene receptor (Vriezen et al., *Plant Journal* 11, 1265–1271 (1997)). Taken together, it may be hypothesized that an analogous signaling chain is operating in the flooded tomato root, utilizing small amounts of the ethylene produced by early flooding-induced ACC synthases to induce Nr and leading to the delayed induction of LE-ACS2. The effect of flooding on the Nr mutant of tomato does not seem to have been analyzed.

At present, it is impossible to assess the relative contribution of the two early ACC synthase genes to the initial burst of ethylene, but the data show that LE-ACS7 plays a role early during flooding. The induction pattern of LE-ACS7 by both flooding and wounding is almost identical, suggesting that this gene has an early and transient function during stress. No previous reports described a wound-inducible tomato gene that could account for the short and transient burst of ethylene produced by wounded leaves. However, prolonged exposure of the leaves to the stress, infection by *Phytophtera infestans*, will induce the LE-ACS2 transcript after two days (Spanu et al., *J. Plant Physiol.* 141, 557–562 (1993)) consistent with the view that LE-ACS2 is a late stress ethylene-gene in vegetative tissues when compared to LE-ACS7.

LE-ACS7 is closely related to ST-ACS2, and their phylogenetic relatedness is not limited to their coding regions but also found in their promoters. The coding regions of both genes are only interrupted by two introns, in contrast to the majority of the ACC synthases with three introns. The sequence identity of these two genes over wide regions of their promoters is unusual and no such strong similarities are detectable between other ACS promoters, not even those of the duplicated ACS genes CP-ACS1A/CP-ACS1B or ST-ACS1A/ST-ACS1B. It is likely that ST-ACS2 and LE-ACS7 evolved from a common ancestor gene and that there exist further close relatives in the Solanaceae. The only ACC synthase promoter cloned from a solanaceous plant other than potato and tomato (PH-ACS1; Genbank accession Nr. PHU64804) does not resemble LE-ACS7 or ST-ACS2. Chloroplast DNA evidence shows that potato and tomato are close relatives, while tobacco is more distant. Tobacco does not contain Sol3 elements (Oosumi, T., Belknap, W. R., *J. Mol. Evol.*, 45, 137–144 (1997a); Oosumi T. and Belknap W. R., *J. Mol. Evol.* 45, 137–144 (1997b)). Thus, the Sol3 transposon has excised from the common ancestor of ST-ACS2 and LE-ACS7 or inserted into the LE-ACS7 promoter only recently. PCR experiments have confirmed the presence of LEACS7Sol3 in both the LE-ACS7 promoters from cv. VF36 (used for the preparation of the genomic library) and cv. UC82 (used for the flooding and wounding experiments). However, further studies will be needed to investigate when the transposition occurred and if and how it affected the flooding and wound-response of tomato plants. The Sol3-element in the tomato PG promoter contributed positive regulatory regions for PG expression and there are a number of cases where it has been shown that the transposition into the promoter altered the plant phenotype (Montgomery et al., 1993; Coen et al., *Cell*, 47, 285–296 (1986); Weil C. F. and Wessler S. R., *Annu. Rev. Plant Physiol. Plant Mol. Biol.*, 41, S27–5S2 (1990)).

ACC synthase gene families should not be seen as a mere case of gene redundancy, but as a case of overlapping gene functions (Mehta P. K. and Christen P., *Biochem.Biophys.Res. Commun.* 198, 138–143 (1994)). The ACC synthase gene LE-ACS7 is part of that family of overlapping functions and plays a role early in the production of stress-ethylene. Recently, transposon-like elements were discovered in the tomato ACC oxidase promoters LE-ACO1 and LE-ACO3 (Blume et al., *Mol. Gen. Genet.*, 254, 297–303 (1997)). Together with the evidence presented here it may be hypothesized that transposable elements may have further and rapidly extended the flexibility of the tomato ethylene biosynthetic gene apparatus and possibly, this may play a role in the root to shoot communication of waterlogged plants.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A recombinant expression cassette comprising an ACS7 promoter operably linked to a heterologous polynucleotide sequence, wherein said promoter is as shown in SEQ ID NO: 1 and is induced in response to flooding.

2. The recombinant expression cassette of claim 1, wherein the heterologous polynucleotide sequence encodes a polypeptide.

3. The recombinant expression cassette of claim 2, wherein the polypeptide confers resistance to a plant pathogen.

4. The recombinant expression cassette of claim 1, wherein the heterologous polynucleotide sequence is operably linked to the ACS7 promoter in the antisense orientation.

5. A recombinant expression vector comprising the expression cassette of claim 1.

6. The recombinant expression vector of claim 5, further comprising an independent terminator sequence, replication sequences and a selection marker sequence.

7. A transgenic plant comprising a recombinant expression cassette comprising an ACS7 promoter operably linked to a heterologous polynucleotide sequence, wherein said promoter is as shown in SEQ ID NO: 1 and is induced in response to flooding.

8. The transgenic plant of claim 7, wherein the heterologous polynucleotide sequence encodes a polypeptide.

9. The transgenic plant of claim 7, wherein the polypeptide confers resistance to a plant pathogen.

10. The transgenic plant of claim 7, wherein the heterologous polynucleotide sequence is operably linked to the ACS7 promoter in the antisense orientation.

11. The transgenic plant of claim 7, which is a tomato.

12. A method of expressing a nucleic acid in a plant, the method comprising providing a transgenic plant comprising a recombinant expression cassette comprising a ACS7 promoter operably linked to a heterologous polynucleotide sequence, wherein said promoter is as shown in SEQ ID NO:1 and is induced in response to flooding; and, subjecting the plant to an environmental stimulus which activates the ACS7 promoter, thereby transcribing the heterologous nucleic acid.

13. The method of claim 12, wherein the environmental stimulus is flooding.

14. The method of claim 12, wherein the environmental stimulus is wounding.

15. The method of claim 12, wherein the heterologous polynucleotide sequence encodes a polypeptide.

16. The method of claim 15, wherein the polypeptide confers resistance to a plant pathogen.

17. The method of claim 12, wherein the heterologous polynucleotide sequence is operably linked to the ACS7 promoter in the antisense orientation.

* * * * *

SEQUENCE LISTING

<160> NUMBER OF SEQ ID NOS: 16

<210> SEQ ID NO 1
<211> LENGTH: 2466
<212> TYPE: DNA
<213> ORGANISM: Lycopersicon esculentum
<220> FEATURE:
<223> OTHER INFORMATION: 1-aminocyclopropane-1-carboxylic acid (ACC)
      synthase (ACS) LE-ACS7 promoter from tomato

<400> SEQUENCE: 1

```
caactatatt tttagcccaa actgagacta agagaggaac aagaatagat ttgagtgggc      60
aacacatagt gaggaaatgg gacaatggca aacaaatgca tggtgactgc tctttaactt     120
ttggatggaa ttatttgtat gtctctttct tctcttccct agtcaacatg taatgtatta     180
agcctatcaa acataaatta cacattttgt tcattccaaa acacaaaaca atgacaagat     240
ctcaagtgcc ctatatgatc tccatttcta atttcaaact tcaatttttt ttttatagag     300
agttgggtcc tttacttttta ttacactatc atatcgacgt ggcttacctc gtgaaataga     360
tcaaaaaaaa ttcatattat tcttattata acttggatta aaaaaaaaca ttttgtatga     420
gttggataac atatttttat atgtattgct gaatattata atcacttatc taattgtaaa     480
atgattatcg aggattacta gtatgaatag aatttctttta aatcttatac ttaaaaagca     540 tgtttttttaa gtctcgaaag gagttacctt tttggtaaga aacgatttta ttttaatgga     600
ttatacgcaa tgtgtatctg aattggtcag gattatgaaa atgttcacac atctagtgag     660
aaattaaaaa aaaattacca tctaataatt taaacggaca agggcctaaa ataccccttaa     720 agtattgaaa atggtacaaa attacccttc attcacctat tgactccaaa atgtcttttt     780
catccaccta ttggctacaa aataccccttg tcatcaacct ttgggttcaa aattgaccat     840
tttttaattg ttataaaatt aaactctttta aatattttttt taaatactgg gcgttcaact     900
attaattata aatttaattt atttatataa tttataaacc aatccactac ccactcatta     960
ctaactaaac ctcactcaat taaatttagg ttgagccgct tatttaggag gacactttct    1020
ttcaaaattg aaaggtaaag aaataataca tcccgaatta attcatgcac ttttttttaaa    1080
```

```
tataatttta taaatattta tgatttattt taaaaccttt aatatattat tttgaaaaaa    1140
agttacctat gaagtaacat cacataattg agacgtaaga ataattaaga tgaacatagt    1200
cagactttta agtttatcgg tgatttttat gtagccactt gaatgtatga taatttactt    1260 ttatatttt taagaacact taattggcag tagcttgcat taataatgtg acgggttcat    1320
ttagagggat ttaattagta atgcgtgggt agtagattga tttataaatt acactgataa    1380
gttaaattat aacaaatagt tgagcaccag gtattttaaa aaatatttaa atagtttaaa    1440
tataaaatcg ttaaataagt ggtcaatttt aaaccaaaag gtggatgaca aaggtatttt    1500
ggacccaata gatggatgag aaaggtattt tgaagccaat aggtggatga agggtaattt    1560
tgtaccattt tcaatacttt gcttaaaata aattatatac tatttgttaa tgtatgtctt    1620
aatttgaagc gggttgaatt gtgcttcttt tagtttataa gttgttacat atttagtgcc    1680
cgcttttaat ttattcaatc ataagtttaa tcaactgaac ttaaatatac ctctgatctt    1740
gtcaaaatac acccaaaaag tttggtcgag tttagatgtt ttcaacactt ctctcgactt    1800
cttattaaga gtcttatgtt catacaagag ttttgagatc atttaatata aatgtgcttt    1860
atcagaagta tatataaatt tagagaattt ttttttaagac tgtcaatgat cgaaaatgac    1920
actaataatt tatgtcaaag tgtattatca atactaaatag aaaatattgg tactaattaa    1980
gtgcagtact atagtagcag actaacagca tcaacattga caataggcag tagcatcacc    2040
aagagtccaa gacatcactt gtcatgtttt tcgaagtgtt tttttaccaa aaatgttgat    2100
gggtgtcaca ttaatgccac ccttttgtta caccctttaga caagccagta caaaattgat    2160
ccaaaatagt ccctacatga catgaaataa aaatattcaa ttataacata cgacgcaaaa    2220
gcgcgtcaac ttagtgtata cttcccaaac acacttaaat taattgtttg tttggagaca    2280
aaaaagtaga aaaaaacaaa aaaatgtata gttaaagttt aaaatcatat ggtgatatgt    2340
ttgtttcttc atccctaaac tcttatatat atatatatac ctcaccatga taaacacat     2400 agcaacaatc ttctctaaat attttctgcc tctcaaaaca aacataaaaa aattcaagtg    2460
caaatg                                                                2466
```

<210> SEQ ID NO 2
<211> LENGTH: 4459
<212> TYPE: DNA
<213> ORGANISM: Lycopersicon esculentum
<220> FEATURE:
<223> OTHER INFORMATION: 1-aminocyclopropane-1-carboxylic acid (ACC) synthase (ACS) LE-ACS7 gene
<221> NAME/KEY: exon
<222> LOCATION: (2464)..(2742)
<221> NAME/KEY: intron
<222> LOCATION: (2743)..(2845)
<221> NAME/KEY: exon
<222> LOCATION: (2846)..(3006)
<221> NAME/KEY: intron
<222> LOCATION: (3007)..(3102)
<221> NAME/KEY: exon
<222> LOCATION: (3103)..(4066)
<221> NAME/KEY: CDS
<222> LOCATION: join(2464..2742, 2846..3006, 3103..4066)

<400> SEQUENCE: 2

```
caactatatt tttagcccaa actgagacta agagaggaac aagaatagat ttgagtgggc      60
aacacatagt gaggaaatgg gacaatggca aacaaatgca tggtgactgc tctttaactt    120
ttggatggaa ttatttgtat gtctctttct tctcttccct agtcaacatg taatgtatta    180
agcctatcaa acataaatta cacattttgt tcattccaaa acacaaaaca atgacaagat    240
```

-continued

```
ctcaagtgcc ctatatgatc tccatttcta atttcaaact tcaattttttt ttttatagag    300
agttgggtcc tttactttta ttacactatc atatcgacgt ggcttacctc gtgaaataga    360
tcaaaaaaaa ttcatattat tcttattata acttggatta aaaaaaaaca ttttgtatga    420
gttggataac atatttttat atgtattgct gaatattata atcacttatc taattgtaaa    480
atgattatcg aggattacta gtatgaatag aatttcttta aatcttatac ttaaaaagca    540
tgttttttaa gtctcgaaag gagttacctt tttggtaaga aacgatttta ttttaatgga    600
ttatacgcaa tgtgtatctg aattggtcag gattatgaaa atgttcacac atctagtgag    660
aaattaaaaa aaaattacca tctaataatt taaacggaca agggcctaaa ataccttaa     720
agtattgaaa atggtacaaa attacccttc attcacctat tgactccaaa atgtcttttt    780
catccaccta ttggctacaa ataccctttg tcatcaacct ttgggttcaa aattgaccat    840
tttttaattg ttataaaatt aaactcttta aatattttt taaatactgg gcgttcaact    900
attaattata aatttaattt atttatataa tttataaacc aatccactac ccactcatta    960
ctaactaaac ctcactcaat taaatttagg ttgagccgct tatttaggag gacactttct   1020
ttcaaaattg aaaggtaaag aaataataca tcccgaatta attcatgcac tttttttaaa   1080
tataatttta taaatattta tgattttattt taaaaccttt aatatattat tttgaaaaaa   1140
agttacctat gaagtaacat cacataattg agacgtaaga ataattaaga tgaacatagt   1200
cagactttta agtttatcgg tgatttttat gtagccactt gaatgtatga aatttactt    1260
ttatattttt taagaacact taattggcag tagcttgcat taataatgtg acgggttcat   1320
ttagagggat ttaattagta atgcgtgggt agtagattga tttataaatt acactgataa   1380
gttaaattat aacaaatagt tgagcaccag gtatttttaaa aaatatttaa atagtttaaa   1440
tataaaatcg ttaaataagt ggtcaatttt aaaccaaaag gtggatgaca aaggtattt    1500
ggacccaata gatggatgag aaaggtattt tgaagccaat aggtggatga agggtaattt   1560
tgtaccattt tcaatactttt gcttaaaata aattatatac tatttgttaa tgtatgtctt   1620
aatttgaagc gggttgaatt gtgcttcttt tagtttataa gttgttacat atttagtgcc   1680
cgcttttaat ttattcaatc ataagtttaa tcaactgaac ttaaatatac ctctgatctt   1740
gtcaaaatac acccaaaaag ttttggtcgag tttagatgtt tcaacacttt ctctcgactt   1800
cttattaaga gtcttatgtt catacaagag ttttgagatc atttaatata aatgtgcttt   1860
atcagaagta tatataaatt tagagaattt ttttaagac tgtcaatgat cgaaaatgac   1920
actaataatt tatgtcaaag tgtattatca atactaatag aaaatattgg tactaattaa   1980
gtgcagtact atagtagcag actaacagca tcaacattga caataggcag tagcatcacc   2040
aagagtccaa gacatcactt gtcatgttttt tcgaagtgtt tttttaccaa aaatgttgat   2100
gggtgtcaca ttaatgccac ccttttgtta caccccttaga caagccagta caaaattgat   2160
ccaaaatagt ccctacatga catgaaataa aaatattcaa ttataacata cgacgcaaaa   2220
gcgcgtcaac ttagtgtata cttcccaaac acacttaaat taattgtttg tttggagaca   2280
aaaaagtaga aaaaaacaaa aaaatgtata gttaaagttt aaaatcatat ggtgatatgt   2340
ttgtttcttc atccctaaac tcttatatat atatatatac ctcaccatga tataacacat   2400
agcaacaatc ttctctaaat attttctgcc tctcaaaaca aacataaaaa aattcaagtg   2460
caa atg aag ctt tta tcg aag aaa gcc atg tgt aac tca cat gga caa    2508
    Met Lys Leu Leu Ser Lys Lys Ala Met Cys Asn Ser His Gly Gln
     1               5                  10                 15
```

```
gat tct tcc tac ttt cta gga tgg gaa gag tat cag aaa aac cca tat      2556
Asp Ser Ser Tyr Phe Leu Gly Trp Glu Glu Tyr Gln Lys Asn Pro Tyr
            20                  25                  30 gat gaa att cgt aat cct aaa gga atc att cag atg ggt ctc gca gag      2604
Asp Glu Ile Arg Asn Pro Lys Gly Ile Ile Gln Met Gly Leu Ala Glu
        35                  40                  45 aat cag ctc tct ttc gat tta tta gag tca tgg ctt act cta aat cca      2652
Asn Gln Leu Ser Phe Asp Leu Leu Glu Ser Trp Leu Thr Leu Asn Pro
    50                  55                  60 gat gca tct gca ttt aag aga aat ggc cac tca ata ttt aga gag ctt      2700
Asp Ala Ser Ala Phe Lys Arg Asn Gly His Ser Ile Phe Arg Glu Leu
65                  70                  75 tcc tta ttt caa gat tac cat ggt ctt cca gct ttc aaa gat                2742
Ser Leu Phe Gln Asp Tyr His Gly Leu Pro Ala Phe Lys Asp
 80                  85                  90 gtaagtttgt gattgcagtc gaatttgact tatatacact gactaacgta actgacttat      2802
catatattta ttattaactt cacaacctca cattgtaatg cag gca ttg gtt caa       2857
                                              Ala Leu Val Gln
                                                           95 ttc atg tct gaa atc aga gga aac aaa gta agc ttt gat tca aat aag      2905
Phe Met Ser Glu Ile Arg Gly Asn Lys Val Ser Phe Asp Ser Asn Lys
            100                 105                 110 ctt gta ctt aca gct ggt gct act tct gca aat gag aca ctc atg ttt      2953
Leu Val Leu Thr Ala Gly Ala Thr Ser Ala Asn Glu Thr Leu Met Phe
        115                 120                 125 tgc ctc gct gat cct ggc cat gct ttc ctc ctt ccc act cca tac tac      3001
Cys Leu Ala Asp Pro Gly His Ala Phe Leu Leu Pro Thr Pro Tyr Tyr
130                 135                 140                 145 cct gg  gtacgtttag tttacactca cattattatt gatcgtctat tttaacacag        3056
Pro Gly ggcgaactat gtactttact aattatgata ttgtgtaata atgcag a ttt gat aga      3112
                                                    Phe Asp Arg
                                                              150 gac tta aaa tgg aga aca gga gct gag att gtt cca ata caa tgc aca      3160
Asp Leu Lys Trp Arg Thr Gly Ala Glu Ile Val Pro Ile Gln Cys Thr
                155                 160                 165 agt tca aac gga ttt aga atc aca gaa tca gct ctt gaa gaa gct tat      3208
Ser Ser Asn Gly Phe Arg Ile Thr Glu Ser Ala Leu Glu Glu Ala Tyr
            170                 175                 180 aca gaa gcc gaa agg cga aac ctt aga gtg aaa ggg gtt tta gtc act      3256
Thr Glu Ala Glu Arg Arg Asn Leu Arg Val Lys Gly Val Leu Val Thr
        185                 190                 195 aac cct tcg aat cca tta ggc aca aca tta acc aaa aaa gaa ctc caa      3304
Asn Pro Ser Asn Pro Leu Gly Thr Thr Leu Thr Lys Lys Glu Leu Gln
    200                 205                 210 ctt ctt ctt acc ttc gta tct aca aaa caa atc cat ctc atc agt gat      3352
Leu Leu Leu Thr Phe Val Ser Thr Lys Gln Ile His Leu Ile Ser Asp
215                 220                 225                 230 gag ata tat tct ggc act gtt ttt aac tca cct aaa ttc gtc agt gtc      3400
Glu Ile Tyr Ser Gly Thr Val Phe Asn Ser Pro Lys Phe Val Ser Val
                235                 240                 245 atg gaa gta cta atc gaa aac aac tac atg tac act gat gta tgg gat      3448
Met Glu Val Leu Ile Glu Asn Asn Tyr Met Tyr Thr Asp Val Trp Asp
            250                 255                 260 aga gtt cac ata gtc tat agt ctt tcg aaa gat ttg gga ctt cca gga      3496
Arg Val His Ile Val Tyr Ser Leu Ser Lys Asp Leu Gly Leu Pro Gly
        265                 270                 275 ttt cga gtt ggt gcc att tat tcc aac gac gat agg gtc gtc tct gca      3544
Phe Arg Val Gly Ala Ile Tyr Ser Asn Asp Asp Arg Val Val Ser Ala
```

```
                280                 285                 290
gcc aca aaa atg tct agt ttt gga tta att tca tct caa act caa tac    3592
Ala Thr Lys Met Ser Ser Phe Gly Leu Ile Ser Ser Gln Thr Gln Tyr
295                 300                 305                 310 ctt ctt tct gct ttg cta tca gac aaa aag ttc acg aaa aat tac gtg    3640
Leu Leu Ser Ala Leu Leu Ser Asp Lys Lys Phe Thr Lys Asn Tyr Val
                315                 320                 325 tct gaa aat caa aag agg ctg aaa aaa cga cat gaa atg cta gtt ggt    3688
Ser Glu Asn Gln Lys Arg Leu Lys Lys Arg His Glu Met Leu Val Gly
            330                 335                 340 ggt ctt aaa caa att gga ata agg tgc ctt gag agc aat gct ggg ttg    3736
Gly Leu Lys Gln Ile Gly Ile Arg Cys Leu Glu Ser Asn Ala Gly Leu
        345                 350                 355 ttt tgt tgg gtg gat atg aga cat ctt tta agt tca aac aca ttt gat    3784
Phe Cys Trp Val Asp Met Arg His Leu Leu Ser Ser Asn Thr Phe Asp
    360                 365                 370 gga gaa atg gaa tta tgg aag aaa ata gtg tac gaa gta ggg cta aat    3832
Gly Glu Met Glu Leu Trp Lys Lys Ile Val Tyr Glu Val Gly Leu Asn
375                 380                 385                 390 att tca gct gga tcg tca tgc cat tgt aca gaa ccg ggt tgg ttt cgt    3880
Ile Ser Ala Gly Ser Ser Cys His Cys Thr Glu Pro Gly Trp Phe Arg
                395                 400                 405 gca tgt ttt gct aac atg tca gaa gat acg tta aat atc gcc ata caa    3928
Ala Cys Phe Ala Asn Met Ser Glu Asp Thr Leu Asn Ile Ala Ile Gln
            410                 415                 420 cgt ttg aag gct ttt gtt gat tca agg gtt aat aac aag gat gat att    3976
Arg Leu Lys Ala Phe Val Asp Ser Arg Val Asn Asn Lys Asp Asp Ile
        425                 430                 435 caa aat cag cag cag tgt tct aat aag aag aag tca ttt tcc aaa tgg    4024
Gln Asn Gln Gln Gln Cys Ser Asn Lys Lys Lys Ser Phe Ser Lys Trp
    440                 445                 450 gtt ttt cga cta tcg ttc aat gaa cgt caa aga gaa cga tag tctagtc    4073
Val Phe Arg Leu Ser Phe Asn Glu Arg Gln Arg Glu Arg
455                 460                 465 atgtgaaagt tcgtaaattc attttgttt ttttaaatct cgatagttaa ttagatgttg    4133
agatttctaa aagattttgt accataatac atactttta attgttttaa ttgtagaggg    4193
tcactgtcca tttgattgga cgagaagtgc ttttccatat acatatggta atacatccat    4253
attattaaat gttcaattaa ttctaattct aatttcagct ctcataaatg aaagataatt    4313
agagaggtga ccgcacaagt gcgtatgcat gctgcgagct cgacctagga gtttcaaggg    4373
acattcggtg aagtctaact caacactagc acccgaggat gctactctga ttcctaggat    4433
atgagagtgc tagatagata tgtgaa                                         4459

<210> SEQ ID NO 3
<211> LENGTH: 467
<212> TYPE: PRT
<213> ORGANISM: Lycopersicon esculentum
<220> FEATURE:
<223> OTHER INFORMATION: 1-aminocyclopropane-1-carboxylic acid (ACC)
      synthase (ACS) LE-ACS7 protein

<400> SEQUENCE: 3

Met Lys Leu Leu Ser Lys Lys Ala Met Cys Asn Ser His Gly Gln Asp
 1               5                  10                  15

Ser Ser Tyr Phe Leu Gly Trp Glu Glu Tyr Gln Lys Asn Pro Tyr Asp
                20                  25                  30

Glu Ile Arg Asn Pro Lys Gly Ile Ile Gln Met Gly Leu Ala Glu Asn
            35                  40                  45
```

```
Gln Leu Ser Phe Asp Leu Leu Glu Ser Trp Leu Thr Leu Asn Pro Asp
     50                  55                  60

Ala Ser Ala Phe Lys Arg Asn Gly His Ser Ile Phe Arg Glu Leu Ser
 65                  70                  75                  80

Leu Phe Gln Asp Tyr His Gly Leu Pro Ala Phe Lys Asp Ala Leu Val
             85                  90                  95

Gln Phe Met Ser Glu Ile Arg Gly Asn Lys Val Ser Phe Asp Ser Asn
            100                 105                 110

Lys Leu Val Leu Thr Ala Gly Ala Thr Ser Ala Asn Glu Thr Leu Met
            115                 120                 125

Phe Cys Leu Ala Asp Pro Gly His Ala Phe Leu Leu Pro Thr Pro Tyr
130                 135                 140

Tyr Pro Gly Phe Asp Arg Asp Leu Lys Trp Arg Thr Gly Ala Glu Ile
145                 150                 155                 160

Val Pro Ile Gln Cys Thr Ser Ser Asn Gly Phe Arg Ile Thr Glu Ser
                165                 170                 175

Ala Leu Glu Glu Ala Tyr Thr Glu Ala Glu Arg Arg Asn Leu Arg Val
            180                 185                 190

Lys Gly Val Leu Val Thr Asn Pro Ser Asn Pro Leu Gly Thr Thr Leu
            195                 200                 205

Thr Lys Lys Glu Leu Gln Leu Leu Leu Thr Phe Val Ser Thr Lys Gln
            210                 215                 220

Ile His Leu Ile Ser Asp Glu Ile Tyr Ser Gly Thr Val Phe Asn Ser
225                 230                 235                 240

Pro Lys Phe Val Ser Val Met Glu Val Leu Ile Glu Asn Asn Tyr Met
                245                 250                 255

Tyr Thr Asp Val Trp Asp Arg Val His Ile Val Tyr Ser Leu Ser Lys
                260                 265                 270

Asp Leu Gly Leu Pro Gly Phe Arg Val Gly Ala Ile Tyr Ser Asn Asp
            275                 280                 285

Asp Arg Val Val Ser Ala Ala Thr Lys Met Ser Ser Phe Gly Leu Ile
            290                 295                 300

Ser Ser Gln Thr Gln Tyr Leu Leu Ser Ala Leu Leu Ser Asp Lys Lys
305                 310                 315                 320

Phe Thr Lys Asn Tyr Val Ser Glu Asn Gln Lys Arg Leu Lys Lys Arg
                325                 330                 335

His Glu Met Leu Val Gly Gly Leu Lys Gln Ile Gly Ile Arg Cys Leu
            340                 345                 350

Glu Ser Asn Ala Gly Leu Phe Cys Trp Val Asp Met Arg His Leu Leu
            355                 360                 365

Ser Ser Asn Thr Phe Asp Gly Glu Met Glu Leu Trp Lys Lys Ile Val
            370                 375                 380

Tyr Glu Val Gly Leu Asn Ile Ser Ala Gly Ser Ser Cys His Cys Thr
385                 390                 395                 400

Glu Pro Gly Trp Phe Arg Ala Cys Phe Ala Asn Met Ser Glu Asp Thr
                405                 410                 415

Leu Asn Ile Ala Ile Gln Arg Leu Lys Ala Phe Val Asp Ser Arg Val
            420                 425                 430

Asn Asn Lys Asp Asp Ile Gln Asn Gln Gln Cys Ser Asn Lys Lys
            435                 440                 445

Lys Ser Phe Ser Lys Trp Val Phe Arg Leu Ser Phe Asn Glu Arg Gln
450                 455                 460
```

Arg Glu Arg
465

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:nuclear
      protein binding region D in the positive regulatory region of the
      polygalacturonase (PG) promoter

<400> SEQUENCE: 4
attkatttat aaattayayy rataagttaa                                      30

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence:nuclear
      protein binding region C in the positive regulatory region of the
      polygalacturonase (PG) promoter

<400> SEQUENCE: 5
atgaacatag t                                                          11

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:nuclear
      protein binding region E in the positive regulatory region of the
      polygalacturonase (PG) promoter

<400> SEQUENCE: 6
attttaaaaa atattwaaww agtttraa                                        28

<210> SEQ ID NO 7
<211> LENGTH: 77
<212> TYPE: DNA
<213> ORGANISM: Lycopersicon esculentum
<220> FEATURE:
<221> NAME/KEY: repeat_region
<222> LOCATION: (1)..(77)
<223> OTHER INFORMATION: Sol3 element long terminal inverted repeat from
      polygalacturonase (PG) gene

<400> SEQUENCE: 7 gaaagggcc taaaatattc tcaaagtatt cgaaatggta caaaactacc atccgtccac      60
ctattgactc caaaata                                                    77

<210> SEQ ID NO 8
<211> LENGTH: 91
<212> TYPE: DNA
<213> ORGANISM: Lycopersicon esculentum
<220> FEATURE:
<221> NAME/KEY: repeat_region
<222> LOCATION: (1)..(91)
<223> OTHER INFORMATION: Sol3 element long terminal inverted repeat from
      polygalacturonase (PG) gene

<400> SEQUENCE: 8
cctactcttc ctataaaact tcggttatac actacctacc tcctattaaa acatagtaag    60
attatgaaat ttctataaaa tccagtaaaa g                                   91

<210> SEQ ID NO 9
<211> LENGTH: 88
<212> TYPE: DNA
<213> ORGANISM: Lycopersicon esculentum
<220> FEATURE:
<221> NAME/KEY: repeat_region
<222> LOCATION: (1)..(88)
<223> OTHER INFORMATION: Sol3 element long terminal inverted repeat from
      LE-ACS7 (LEACS7Sol3)

<400> SEQUENCE: 9
ggacaagggc ctaaaatacc cttaaagtat tgaaaatggt acaaaattac ccttcattca      60
cctattgact ccaaaatgtc ttttcat                                         88

<210> SEQ ID NO 10
<211> LENGTH: 90
<212> TYPE: DNA
<213> ORGANISM: Lycopersicon esculentum
<220> FEATURE:
<221> NAME/KEY: repeat_region
<222> LOCATION: (1)..(90)
<223> OTHER INFORMATION: Sol3 element long terminal inverted repeat from
      LE-ACS7 (LEACS7Sol3)

<400> SEQUENCE: 10
cctactgttt ccataaaacc tgggttatct acctactctt tccataaaac ttcggttatc      60
cacctacttc ccattaaaac atggtaaaag                                      90

<210> SEQ ID NO 11
<211> LENGTH: 90
<212> TYPE: DNA
<213> ORGANISM: Solanum tuberosum
<220> FEATURE:
<221> NAME/KEY: repeat_region
<222> LOCATION: (1)..(90)
<223> OTHER INFORMATION: Sol3 element long terminal inverted repeat from
      Potten 1

<400> SEQUENCE: 11 gtaaagggc ctaaaatatc ctcgaagtat tggaaaatga tacaaaagta ccctacatcc       60
acctattggc tcaaaatgcc cttctcatcc                                      90

<210> SEQ ID NO 12
<211> LENGTH: 84
<212> TYPE: DNA
<213> ORGANISM: Solanum tuberosum
<220> FEATURE:
<221> NAME/KEY: repeat_region
<222> LOCATION: (1)..(84)
<223> OTHER INFORMATION: Sol3 element long terminal inverted repeat from
      Potten 1

<400> SEQUENCE: 12
cctactcttc ccataaaacc tcggtatcca cctaccatca aaaatggta aagattatga       60 agttcccata aaatctggta aaag                                            84

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:
      amplification primer A
<221> NAME/KEY: modified_base
<222> LOCATION: (20)
<223> OTHER INFORMATION: n = g, a, c or t

```
<400> SEQUENCE: 13
ayccwtswaa tccaytrggn ac                                              22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      amplification primer B
<221> NAME/KEY: modified_base
<222> LOCATION: (6)
<223> OTHER INFORMATION: n = g, a, c or t
<221> NAME/KEY: modified_base
<222> LOCATION: (15)
<223> OTHER INFORMATION: n = g, a, c or t

<400> SEQUENCE: 14
acwarnccra arctngacat                                                 20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:genomic DNA
      amplification primer C

<400> SEQUENCE: 15
catggctagc acaaaatcca ga                                              22

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence:genomic DNA
      amplification primer D

<400> SEQUENCE: 16
tacactgatg tatgggatag agttca                                          26
```